United States Patent [19]
Oliveira

[11] Patent Number: 5,531,753
[45] Date of Patent: Jul. 2, 1996

[54] SURGICAL CORRECTION OF ASTIGMATISM

[75] Inventor: Canrobert Oliveira, Brasilia, Brazil

[73] Assignee: Philip Stephen Cantor, Brasilia, Brazil; a part interest

[21] Appl. No.: 292,517

[22] Filed: Aug. 18, 1994

[51] Int. Cl.⁶ .............................. A61F 9/00; A61B 19/00
[52] U.S. Cl. ........................... 606/166; 128/898; 30/358; 30/316
[58] Field of Search ...................................... 606/166, 167; 33/512, 507, 669; 30/164.9, 358, 316; 128/898

[56] References Cited

U.S. PATENT DOCUMENTS

| | | | |
|---|---|---|---|
| 4,417,579 | 11/1983 | Soloviev et al. | 33/512 |
| 4,515,157 | 5/1985 | Fedorov et al. | 606/166 |
| 4,705,053 | 11/1987 | Givens | 606/116 |
| 4,739,761 | 4/1988 | Grandon | 606/166 |

FOREIGN PATENT DOCUMENTS

| 1554910 | 4/1990 | U.S.S.R. | 606/166 |
|---|---|---|---|

OTHER PUBLICATIONS

Thornton, Ch. 5 in the book entitled "Radial Keratotomy Surgical Techniques", edited by Donald R. Sanders M.D., PhD, published by Slack, Inc., Thorofare, NJ, 1986.
Lindquist et al., Ch. 6 in the book entitled "Radial Keratotomy Surgical Techniques", idem . . . .
Hofmann, Ch. 14 in the book entitled "Refractive Corneal Surgery", edited by Donald R. Sanders M.D., PhD; Robert F. Hoffman, M.D.; and James J. Salz, published by Slack, Inc., Thorofare, NJ, 1986.
Lindstrom, Linsdstrom Nomogram, published by Chiron Opthalmics, 1990.
Ellis, William, M.D., F.A.C.S., pp. 27 and 28 in the book entitled "Radial Keratotomy and Astigmatism Surgery", published by Keith C. Terry & Associates Medical Textbook Division, Irvine, CA 1986.
Copy of 2-sided advertisement entitled "Magnificent Markers"by Mastel.

*Primary Examiner*—Michael H. Thaler
*Assistant Examiner*—Scott B. Markow

[57] ABSTRACT

A surgical procedure to correct astigmatism comprises performing a first pair of incisions across the cornea's steepest meridian at a first optical zone and an additional two to four incisions across the bisector meridians at a second optical zone that is greater than that of the first optical zone. This procedure is effective to improve astigmatism up to 6D without many of the detrimental effects of the known procedures. The invention further comprises a set of markers to be used by a surgeon for marking on the cornea the pattern of incisions to be made following the procedure of the invention.

26 Claims, 4 Drawing Sheets

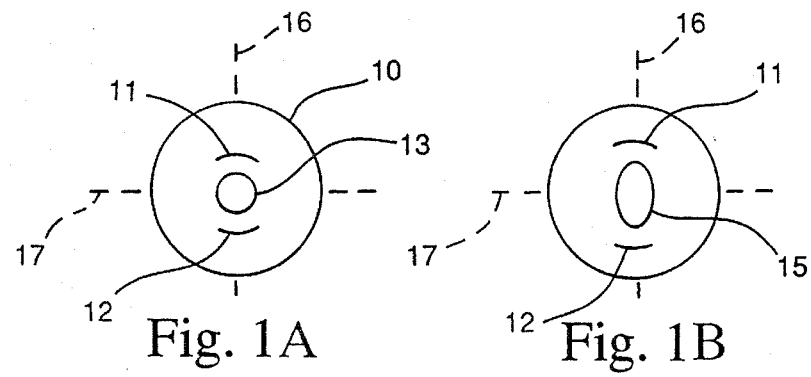
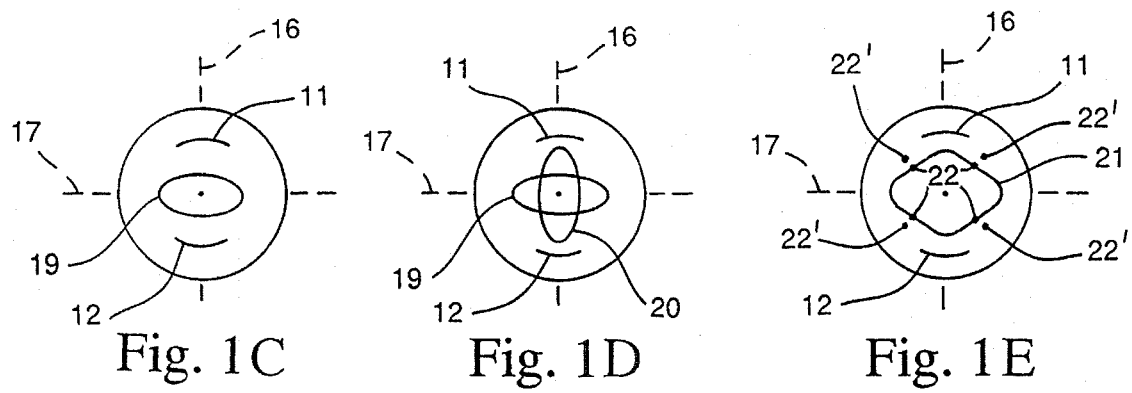
Fig. 1A   Fig. 1B   Fig. 1C   Fig. 1D   Fig. 1E
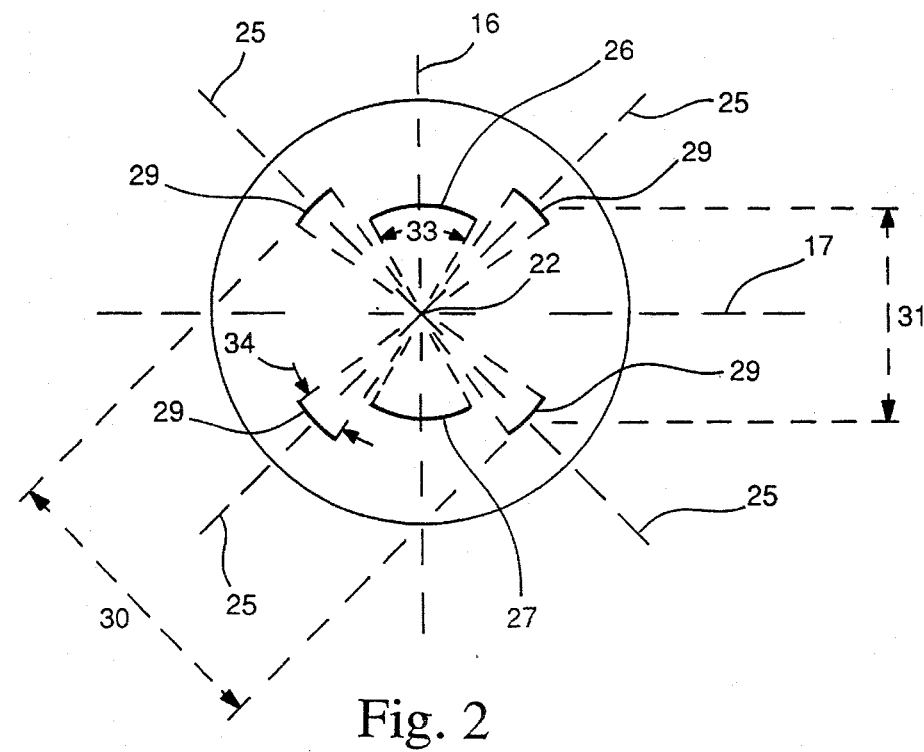
Fig. 2

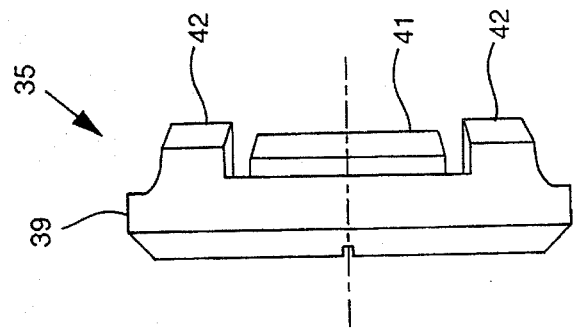
Fig. 4A
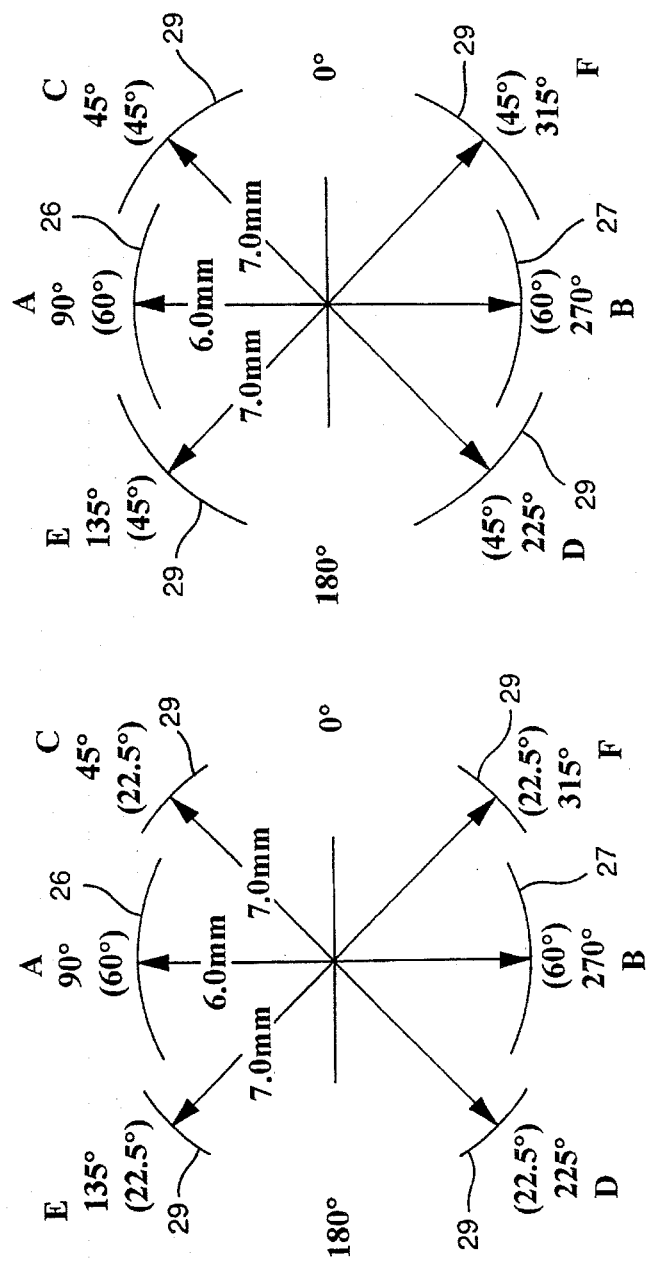
Fig. 3E
Fig. 3D

SURGICAL CORRECTION OF ASTIGMATISM

BACKGROUND OF THE INVENTION

This invention relates to a medical procedure for correcting astigmatism by the execution of corneal incisions, and to marking devices for use in carrying out such procedures.

For a clearer understanding of the invention, a number of terms, in double quotes, will be defined, and it is understood that when those terms are used hereinafter in the specification or the claims they will have the meanings as herein defined.

A normal cornea is spherical and positions are located by equal meridians analogous to great circles on the surface of a globe. An astigmatic cornea is shaped similar to a USA football and has unequal meridians. The "steepest" meridian is the steepest or most curved meridian of the astigmatic cornea. The "secondary" meridian is the flattest and least curved meridian that is always transverse to or rotated 90° with respect to the steepest meridian. For convenience of explanation, unless otherwise indicated, the steepest meridian will be considered to extend in the North (N) to South (S) direction and the secondary meridian in the West (W) to East (E) direction. The "bisector" meridians are the meridians which divide in two equal parts the quadrants between the steepest and secondary meridians, of which two exist: NW to SE and SW to NE. The "surgical" meridian is the meridian which passes through the center of transverse or arcuate incisions in the cornea and should always coincide with the steepest meridian unless it is executed improperly and thus extends along a line offset from the steepest meridian. The "axis of a meridian" is the straight line extending through the end points of the meridian.

When a circular light is projected over an astigmatic cornea, an oval reflection is produced called an "oval keratometric mire". When it is horizontal like the eye opening, the astigmatism is "with the rule"; when vertical, it is "against the rule". The "optical zone", is the area of the cornea through which light rays can pass through the pupil to the retina, and the "optical axis" is the axis passing through the center of the optical zone. The optical zone is measured in millimeters (mm) of its diameter and is typically about 5 mm in an adult. "Markers" are surgical instruments used by the surgeon to mark positions on the patient's cornea to assist the surgeon in locating the precise lines where incisions are to be performed. Typically, markers comprise a handle having at the distal working end an angled circular structure with projecting thin edges—also sometimes with crosshairs for aiming—which are pressed against the cornea after proper positioning to leave a visible mark or marks that the surgeon can use to locate the incisions. They are typically sold in sets wherein the working ends are scaled in size for use with patients with different degrees of astigmatism.

To correct astigmatism, which means to transform an astigmatic cornea into as nearly a spherical one as possible, various surgical techniques have been developed which are characterized by the execution of relaxing surgical incisions on opposite sides of the optical axis across the steepest meridian, the most curved part of the cornea. The underlying concept is that the incisions across the steepest meridian will cause the cornea to flatten along that meridian, thus tending to bring the curvature of the meridians closer together, hence shape the cornea more spherically. Most recommended surgical procedures have formed straight lines running parallel to the steepest meridian, or transverse to the steepest meridian, or both. One procedure recommended a pair of arcuate (segments of an arc) incisions from 45°–90° across the steepest meridian on opposite sides of the optical axis. These known surgical techniques have suffered from various drawbacks in that they not only have been less than fully successful in correcting many forms of astigmatism, but also have on occassion introduced new distortions in the patient's vision.

SUMMARY OF THE INVENTION

An object of the invention is an improved procedure for surgically reshaping the cornea to reduce astigmatism.

Another object of the invention is a novel set of markers for carrying out the procedure of the invention.

The invention is based upon the following new understandings and discoveries. The known procedures have produced certain undesirable effects. The first undesirable effect is the persistence after the surgery of astigmatism with an axis oriented in a different direction, however small the variations between the steepest meridian and the surgical meridian. The second undesirable effect is the ineffectiveness of the correction in one of the hemispheres of the steepest meridian, which tends to generate a new astigmatism 90° away from the one which the surgery intended to correct. The third undesirable effect is the ineffectiveness of the correction in both hemispheres of the steepest meridian, generating a consistent yatrogenic (human induced) alteration in the center of the cornea which I designate "Keratopyramis", having the geometric form of a pyramid with the pyramid apex over a quadrilateal or triangular base. I believe that Keratopyramis occurs because the relaxing effect of the transverse or arcuate incisions is always more intense along the steepest meridian than in the areas surrounding the bisector meridians. I have found that a different set of incisions than had been used heretofore affords a distinct improvement in astigmatism correcting procedures avoiding one or more of the undesirable effects described above.

In accordance with a first aspect of the invention, my novel surgical procedure comprises performing a first set comprising a pair of incisions across the steepest meridian at a first optical zone as was used heretofore, but adding to the first set an additional second set comprising from two up to four incisions across the bisector meridians at a second optical zone that is greater than that of the first optical zone.

In accordance with another aspect of the present invention, the first set of incisions are preferably arcuate, and the second set of incisions are preferably arcuate or C-shaped. In a preferred embodiment according to the invention, the arc length of the first set of incisions varies between about 43°–62°, and that of the second set of incisions varies between about 20°–47°, depending on the degree of correction desired. Preferably, the optical zone for the first set of incisions varies between about 5.8–7.7 mm, and that of the second set of incisions varies between about 6.8–8.7 mm, also depending on the degree of correction desired. As will be noted, "optical zone" is used here to mean surgical zone, i.e., the location of the incisions.

The various features of novelty which characterize the invention are pointed out with particularity in the claims annexed to and forming a part of this disclosure. For a better understanding of the invention, its operating advantages and specific objects attained by its use, reference should be made to the accompanying drawings and descriptive matter in which there are illustrated and described the preferred embodiments of the invention, in which drawings like references denote like or corresponding parts.

BRIEF DESCRIPTION OF THE DRAWINGS

FIGS. 1A–1E are sketches of the cornea illustrating the effect of arcuate incisions on the cornea, wherein: FIGS. 1A and 1B represent the same cornea, preop and postop; FIG. 1C represents a preop astigmatic cornea; and FIGS. 1D and 1E represent the same astigmatic cornea postop;

FIG. 2 is a front view of a typical cornea showing the location of incisions in accordance with one form of the procedure of the invention;

FIGS. 3A–3E are front views of corneas showing the locations and sizes of incisions following the procedure of the invention for correcting different degrees of astigmatism;

FIGS. 4A–4C are side, rear, and front views, respectively, of one form of marker in accordance with the invention.

DETAILED DESCRIPTION OF THE PREFERRED EMBODIMENTS

Figures 3A, 3B, 3C:
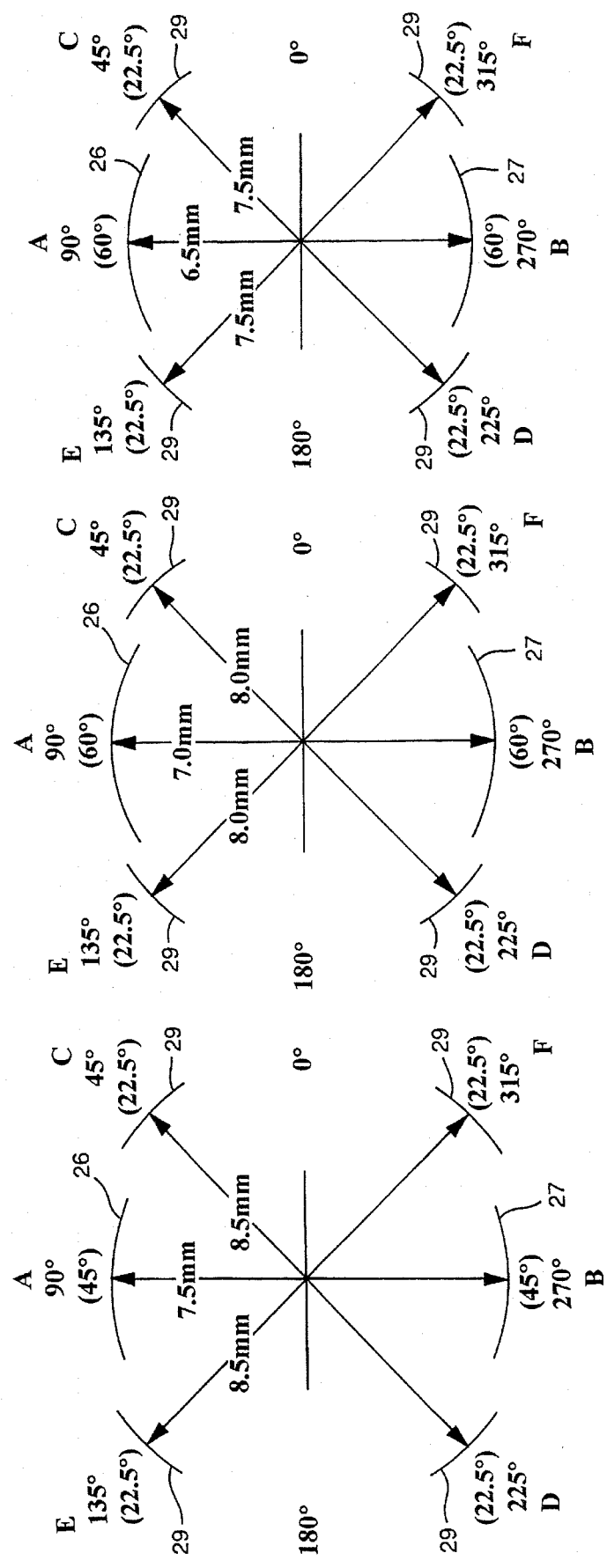

My invention will be better understood with a further explanation of how Keratopyramis arises. If two equidistant incisions 11, 12 from the circular mire 13 are made in a spherical cornea 10 as shown in FIG. 1A, a relaxation of the surgical meridian occurs which has the effect of of transforming a spherical cornea into an astigmatic cornea against the rule as shown by the oval mire at 15 in FIG. 1B, because the relaxation causes the surgical meridian 16 to become flatter than the meridian 17 rotated 90° away. If the same incisions are made in an astigmatic cornea with the rule as shown at 19 in FIG. 1C, the effect will be to produce an astigmatism against the rule as shown at 20 in FIG. 1D. The result of these alterations will be a quadralateral mire 21, which is the summation of the two oval keratometric mires 19, 20 of the original astigmatism with the rule and the one against the rule induced by the surgeon, as shown in FIG. 1E. This quadralateral mire forms the base of the Keratopyramis depicted in FIG. 1E.

To correct the Keratopyramis, i.e., to restore the curve 21 to a circle, indicative of a return to sphericity, my invention provides a more intense effect in the areas surounding the bisector meridians at a greater optical zone in order to dislocate the points indicated by 22 to further outward positions indicated by the corresponding primed points 22'. FIG. 2 shows at 26 and 27 the paired arcuate keratotomy as before, and reference numeral 29 denotes four arcuate or C incisions on the bisector meridians at the greater optical zone in accordance with my invention. The optical zone for the first set of incisions is designated 31, and that for the second set of incisions is designated 30. It will be noted that the optical zone 30 is larger than the optical zone 31. The arc length of each of the first set of incisions, 26, 27, is designated 33, and that for each of the second set of incisions is designated 34. As before, the steepest meridian is designated 16, and the flattest meridians are designated 17. The bisector meridians are designated 25.

The incision are lengths and their location depends upon the degree of astigmatism to be corrected. FIGS. 3A–3E show on an enlarged scale the locations and sizes for both sets of incisions in accordance with the invention. Each of the arcs is labelled with a letter A–F. In FIGS. 3A–3E the steepest meridian is located along the axis running from the 90° to the 270° position, and the bisector meridians run from 45° to the 225° and from 135° to the 315° position. The angles in parentheses are the angles subtending arc lengths of the incisions, and the numbers in mm along the double-arrowed lines are the respective optical zones of the incisions. FIGS. 3A–3E are the incision positions and sizes for an astigmatic correction of 2, 3, 4, 5, and 6 diopters (D), respectively. The table (nomogram) below lists the optical zones and arc lengths for the different corrections.

| CANROBERT "C" PROCEDURE NOMOGRAM FOR ASTIGMATISM* | | | | | |
|---|---|---|---|---|---|
| Diopters | 2D | 3D | 4D | 5D | 6D |
| Optical Zone Diameter for First Set of Incisions (mm) | 7.5 | 7.0 | 6.5 | 6.0 | 6.0 |
| Arc Length of First Set of Incisions (degrees) | 45 | 60 | 60 | 60 | 60 |
| Optical Zone Diameter for Second Set of Incisions (mm) | 8.5 | 8.0 | 7.5 | 7.0 | 7.0 |
| Arc Length of Second Set of Incisions (degrees) | 22.5 | 22.5 | 22.5 | 22.5 | 45 |

*For patients below 40 years of age. At or above 40 years of age, increase the optical zone by 0.5 mm.

While best results have been obtained with arcuate incisions that are arcs or segments of a circle, it will be understood that the invention is not limited to arcuate incisions. I believe that satisfactory results will also be obtained with straight incisions substantially transverse to the relevant meridians of the same lengths and optical zones specified in the nomogram above.

Similarly, while best results are obtained with the arc lengths and positions substantially as shown in FIGS. 3A–3E, it will also be understood that minor variations in those dimensions should not significantly affect the results. So, for example, the arc lengths could vary up to about 2° and the optical zones could vary up to about ±0.2 mm. Thus, for example, where the arc length is given as 60° it can vary from about 58°–62°; and where given as 22.5° it can vary from about 20.5°–24.5°. Similarly, where the optical zone is given as 6 mm it can vary from about 5.8–6.2 mm; and where the optical zone is given as 8.5 mm it can vary from about 8.3–8.7 mm. Corresponding changes are allowable in the other dimensions given.

As far as the depth of the incisions are concerned, for both sets, the depth is chosen in the conventional manner to be about 100% of the value of the thickness at the center of the cornea. The latter value is conventionally measured with an ultrasonic pachymeter. The incision depth can vary between about 98–102% of the measured thickness value.

Figure 4C:
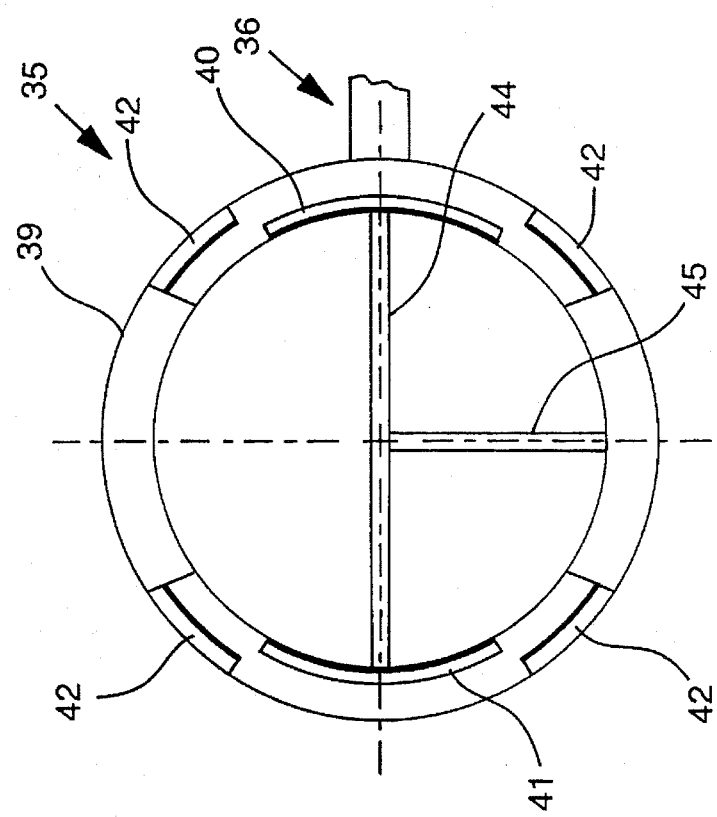
Figure 4B:
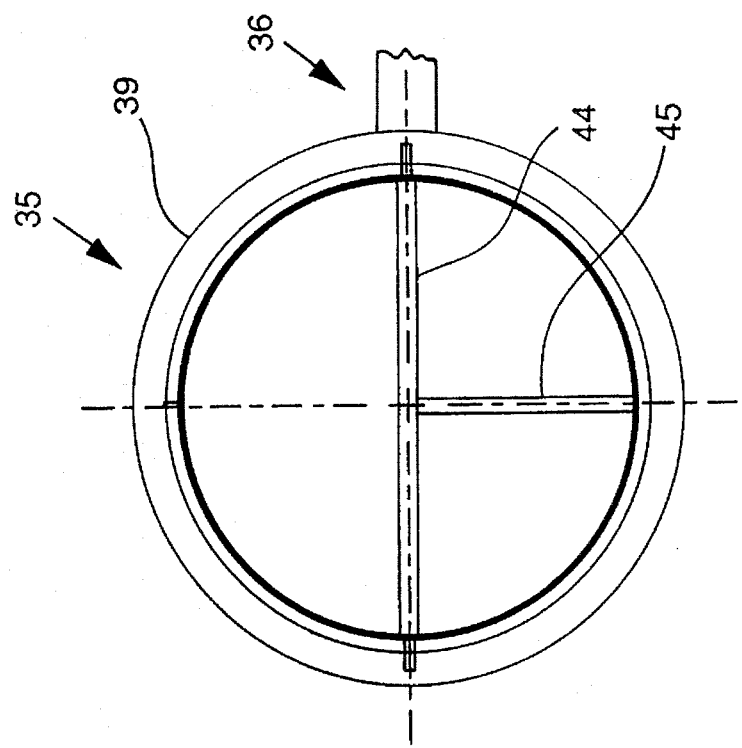

In carrying out the surgical procedure, markers are used to make a pattern of marks on the cornea where the surgeon is to make the incisions desired. In the traditional procedure, the surgeon places the marker over the steepest meridian, i.e., the primary meridian, of the patient's cornea in such a way that the steepest meridian divides the face of the marker into two symetrically equal parts. When the marker is in the correct position, the surgeon presses it onto the cornea to make a pattern of surgical marks over which he or she will subsequently make incisions as shown in one of FIGS. 3A–3E. Thus, the active marker face, herein also called the marker front, will have thin edges that mimic the pattern of incisions shown in FIGS. 3A–3E. FIGS. 4A–4C show side, rear, and front views, respectively, of a typical marker 35 according to the invention. The marker handle 36, only part of which is shown only in FIGS. 4B and 4C, extends about 8–14 mm to provide a convenient length by which the surgeon can hold the marker while observing its position relative to the patient's cornea located opposite the marker front side shown in FIG. 4C. The working end of the marker comprises an annular body 39, typically of surgical steel, which comprises at its front side arcuate thin edges. In this case, a pair of opposed thin edges 40, 41 are provided at positions corresponding to the first set 26, 27 of incisions to be made. In addition, a second set of thin edges 42 are provided at positions corresponding to the second set of incisions 29 to be made. The second set of edges 42 protrudes slightly more to take into account the cornea curvature. A separate marker would be provided for each of the incision patterns shown in FIGS. 3A–3E, thus a total of five. A full set of such markers would be available to a surgeon performing procedures for the surgical correction of astigmatism.

As shown in FIGS. 4B and 4C, in accordance with another aspect of the invention, the marker has one full crosshair 44 extending as a diameter across the annular body in the direction of the handle, and another half crosshair 45, rotated 90° with respect to the full crosshair 44, on the left side at the rear view (the surgeon's view) FIG. 4B. The half crosshair 45 extends as a radius from the center of the full crosshair 44 to the edge of the annular body. I have found that the full and half crosshairs provide an improved positioning system that greatly assists the surgeon in positioning the marker over the cornea.

For further background as to the details of various surgical procedures and the instruments used to correct astigmatism, reference is made to the following publications, whose contents are herein incorporated by reference:

Thornton, Ch. 5 in the book entitled "Radial Keratotomy Surgical Techniques" edited by Donald R. Sanders M.D., PhD, published by Slack, Inc., Thorofare, N.J., 1986.

Lindquist et al., Ch. 6 in the book entitled "Radial Keratotomy Surgical Techniques"; idem . . .

Hofmann, Ch. 14 in the book entitled "Refractive Corneal Surgery", edited by Donald R. Sanders M.D., PhD; Robert F. Hofmann, M.D.; and James J. Saltz, published by Slack, Inc., Thorofare, N.J., 1986.

Ellis, William, M.D., F.A.C.S., pages 27 and 28 in the book entitled "Radial Keratotomy and Astigmatism Surgery", published by Keith C. Terry & Associates Medical Textbook Division, Irvine, Calif., 1986.

Lindstrom, Linsdstrom Nomogram, published by Chiron Opthalmics, 1990;

Copy of 2-sided advertisement entitled "Magnificent Markers" by Mastel.

The procedures described herein have had excellent success. The surgical results are typically measured before and after surgery by corneal topography, which produces color maps of the cornea which show via different colors the degree of steepness of the cornea surface. Typically, the warm colors (red and orange) represent the more curved areas and the cool colors (blue and green) the less curved areas. The colors can be mapped to various diopters. The difference in curvature between the steepest and flattest meridians is what determines astigmatism and its degree, measured in diopters. An improvement in astigmatism is demonstrated by corneal topography in which generally the warm colors before surgery disappear and are replaced after surgery by cool blue colors which are closer in tone, meaning that great differences in curvature have been eliminated and that the cornea is now more spherical. Many patients that I have treated with the procedures described herein have uniformly been shown to have corneas with improved—and in many cases optimal—sphericity without the undesirable effects described above in connection with FIG. 1. The procedures described herein provides surgical correction of astigmatism with the following advantages:

a) more effective up to 6 diopters;

b) more anatomical;

c) more physiological;

d) increased coupling effect;

e) greater correction of hyperopic astigmatism;

f) less incidence of yatrogenic effects.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A surgical procedure for correcting astigmatism, comprising:

(a) executing on the cornea a first set of incisions comprising two opposed incisions generally transverse to the steepest meridian along a first optical zone, (b) executing on the cornea a second set of incisions comprising from two to four incisions each generally transverse to a bisector meridian along a second optical zone which is larger than the first optical zone.

2. The surgical procedure of claim 1, wherein the second set of incisions comprises four incisions.

3. The surgical procedure of claim 2, wherein the first and second sets of incisions are arcuate.

4. The surgical procedure of claim 2, wherein the first and second sets of incisions are straight.

5. The surgical procedure of claim 2, wherein the first set of incisions extend over an optical zone whose diameter is about 6–7.5 mm.

6. The surgical procedure of claim 2, wherein the second set of incisions extend over an optical zone whose diameter is about 7–8.5 mm.

7. The surgical procedure of claim 2, wherein the first set of incisions each extend over an angular range that is about 45°–60°.

8. The surgical procedure of claim 2, wherein the second set of incisions each extend over an angular range that is about 22.5°–45°.

9. The surgical procedure of claim 2 for correcting 2D astigmatism, wherein the first set of incisions are made in an optical zone of about 7.5 mm in diameter and are each about 45° in arcuate length, and the second set of incisions are made in an optical zone of about 8.5 mm in diameter and are each about 22.5° in arcuate length.

10. The surgical procedure of claim 2 for correcting 3D astigmatism, wherein the first set of incisions are made in an optical zone of about 7.0 mm in diameter and are each about 60° in arcuate length, and the second set of incisions are made in an optical zone of about 8.0 mm in diameter and are each about 22.5° in arcuate length.

11. The surgical procedure of claim 2 for correcting 4D astigmatism, wherein the first set of incisions are made in an optical zone of about 6.5 mm in diameter and are each about 60° in arcuate length, and the second set of incisions are each made in an optical zone of about 7.5 mm in diameter and are each about 22.5° in arcuate length.

12. The surgical procedure of claim 2 for correcting 5D astigmatism, wherein the first set of incisions are made in an optical zone of about 6.0 mm in diameter and are each about 60° in arcuate length, and the second set of incisions are made in an optical zone of about 7.0 mm in diameter and are each about 22.5° in arcuate length.

13. The surgical procedure of claim 2 for correcting 6D astigmatism, wherein the first set of incisions are made in an optical zone of about 6.0 mm in diameter and are each about 60° in arcuate length, and the second set of incisions are each made in an optical zone of about 7.0 mm in diameter and are each about 45° in arcuate length.

14. The surgical procedure of claim 2 for correcting different degrees in diopters of astigmatism by incisions of lengths and at optical zones as set forth in the table below:

| Diopters | 2D | 3D | 4D | 5D | 6D |
|---|---|---|---|---|---|
| Optical Zone Diameter for First Set of Incisions (mm) | 7.5 | 7.0 | 6.5 | 6.0 | 6.0 |
| Arc Length of First Set of Incisions (degrees) | 45 | 60 | 60 | 60 | 60 |
| Optical Zone Diameter for Second Set of Incisions (mm) | 8.5 | 8.0 | 7.5 | 7.0 | 7.0 |
| Arc Length of Second Set of Incisions (degrees) | 22.5 | 22.5 | 22.5 | 22.5 | 45, | for patients at or above 40 years of age, increase both optical zone diameters by 0.5 mm.

15. In a surgical marker for marking the positions of corneal incisions in a surgical procedure for correcting astigmatism, wherein said marker comprises a handle having at one end means for marking the cornea when pressed thereon, the improvement wherein said means for marking has a generally annular shape having 45°, 90°, 135°, 225°, 270°, and 315° axes and comprises:

(a) a first set of marking edges comprising two opposed marking edges each generally transverse to one of the 90° and 270° axes and spaced apart by a first predetermined distance, (b) a second set of marking edges comprising four marking edges each generally transverse to one of the 45°, 135°, 225°, and 315° axes and forming two pairs of opposed marking edges with each pair spaced apart by a second predetermined distance that is greater than the first predetermined distance.

16. The surgical marker of claim 15, wherein the first and second sets of marking edges are arcuate.

17. The surgical marker of claim 15, wherein the first and second sets of marking edges are straight.

18. The surgical marker of claim 15, wherein the first predetermined distance is about 6–7.5 mm.

19. The surgical marker of claim 15, wherein the second predetermined distance is about 7–8.5 mm.

20. The surgical marker of claim 15, wherein the first set of marking edges each extend over an angular range that is about 45°–60°.

21. The surgical marker of claim 15, wherein the second set of marking edges each extend over an angular range that is about 22.5°–45°.

22. The surgical marker of claim 15 for correcting 2D astigmatism, wherein the first set of marking edges are spaced apart about 7.5 mm and are each about 45° in arcuate length, and the second set of marking edges are spaced apart about 8.5 mm and are each about 22.5° in arcuate length.

23. The surgical marker of claim 15 for correcting 3D astigmatism, wherein the first set of marking edges are spaced apart about 7.0 mm and are each about 60° in arcuate length, and the second set of marking edges are spaced apart about 8.0 mm and are each about 22.5° in arcuate length.

24. The surgical marker of claim 15 for correcting 4D astigmatism, wherein the first set of marking edges are spaced apart about 6.5 mm and are each about 60° in arcuate length, and the second set of marking edges are spaced apart about 7.5 mm and are each about 22.5° in arcuate length.

25. The surgical marker of claim 15 for correcting 5D astigmatism, wherein the first set of marking edges are spaced apart about 6.0 mm and are each about 60° in arcuate length, and the second set of marking edges are spaced apart about 7.0 mm and are each about 22.5° in arcuate length.

26. The surgical marker of claim 15 for correcting 6D astigmatism, wherein the first set of marking edges are spaced apart about 6.0 mm and are each about 60° in arcuate length, and the second set of marking edges are spaced apart about 7.0 mm and are each about 45° in arcuate length.

* * * * *